(12) United States Patent
Rodriguez et al.

(10) Patent No.: US 8,658,214 B2
(45) Date of Patent: Feb. 25, 2014

(54) METHODS FOR PROCESSING MICROSPHERES

(75) Inventors: Oscar Rodriguez, Pembroke Pines, FL (US); Roberto Candelaria, Homestead, FL (US)

(73) Assignee: Scion Cardio-Vascular, Inc., Miami, FL (US)

( * ) Notice: Subject to any disclaimer, the term of this patent is extended or adjusted under 35 U.S.C. 154(b) by 0 days.

(21) Appl. No.: 13/247,287

(22) Filed: Sep. 28, 2011

(65) Prior Publication Data

US 2012/0082733 A1 Apr. 5, 2012

Related U.S. Application Data

(60) Provisional application No. 61/387,789, filed on Sep. 29, 2010.

(51) Int. Cl.
*A61K 9/14* (2006.01)

(52) U.S. Cl.
USPC .......................................................... 424/489

(58) Field of Classification Search
USPC .......................................................... 424/489
See application file for complete search history.

(56) References Cited

U.S. PATENT DOCUMENTS

| | | | |
|---|---|---|---|
| 4,981,625 A | * | 1/1991 | Rhim et al. ..................... 264/13 |
| 6,680,046 B1 | * | 1/2004 | Boschetti ....................... 424/9.1 |
| 7,094,369 B2 | | 8/2006 | Buiser et al. |
| 7,105,158 B1 | | 9/2006 | D'Souza et al. |
| 7,591,993 B2 | | 9/2009 | Boschetti |
| 2008/0274161 A1 | | 11/2008 | Muratoglu et al. |
| 2008/0317866 A1 | | 12/2008 | Chan et al. |

FOREIGN PATENT DOCUMENTS

WO 2012050879 4/2012

OTHER PUBLICATIONS

International Search Report for PCT/US2011/053644 filed Sep. 28, 2011 (WO2012/050879).

* cited by examiner

*Primary Examiner* — Ali Soroush
(74) *Attorney, Agent, or Firm* — Fleit Gibbons Gutman Bongini & Bianco PL; Paul D. Bianco; Martin Fleit

(57) ABSTRACT

The invention provides a manufacturing method for processing polymeric microspheres which are suspended in a liquid. The invention also provides polymeric microspheres produced by the method which can be used in medical settings as tissue fillers, tissue bulking agents, embolization agents, and/or as drug delivery agents.

31 Claims, 6 Drawing Sheets

METHODS FOR PROCESSING MICROSPHERES

CROSS REFERENCE TO RELATED APPLICATIONS

This application claims the benefit of priority to U.S. Provisional Patent Application No. 61/387,789, filed on Sep. 29, 2010, the content of which is hereby incorporated in its entirety.

FIELD OF THE INVENTION

The invention generally relates to methods for preparing polymeric microspheres which can be used in a variety of medical applications, particularly to a manufacturing method for processing polymeric microspheres which are suspended in a liquid, and mostly particularly, to a manufacturing method for processing polymeric microspheres or irregular shaped particles, in which the polymer or copolymer is Polyvinyl Alcohol (PVA), Polyvinyl Alcohol Acrylate, Polyvinyl Acetate (PVAc), or other copolymers using PVA.

BACKGROUND OF THE INVENTION

The processing of Polyvinyl Alcohol (PVA) to manufacture spheres or irregular shape particles that would be suspended in an aqueous fluid carrier, such as 0.9% Sodium Chloride (Saline), requires the PVA material to undergo a crosslink process to change its inherent water solubility property.

Typical crosslink processes for PVA, not only affect the water solubility of the PVA, but also the material's physical properties such as flexibility, compressibility, softness, fluid absorption capabilities, and other physical properties which may be desired in the final PVA product. In order to avoid, minimize, or control some of these physical property changes on PVA spheres and/or particles, the methods of the present invention allow cross-linking of the PVA polymer to make the PVA insoluble in water or other fluid carrier without significant loss or changes to its other inherent physical properties, in particular, the spheres/particle flexibility, compressibility, softness, and fluid absorption capabilities.

SUMMARY OF THE INVENTION

The invention provides both a manufacturing method for processing microspheres suspended in liquid and polymeric microspheres processed by this method. The polymeric microspheres can be used in medical settings as tissue fillers, tissue bulking agents, embolization agents, and/or as drug delivery agents.

Although the microspheres are preferably processed using polyvinyl alcohol (PVA), the invention is not limited to the use of PVA material. The inherent water solubility of polyvinyl alcohol must be altered to prepare microspheres. This is typically achieved using crosslinking techniques.

Some of the chemicals used in chemical crosslinking of polymers for microsphere formation are cytotoxic, irritating, or even possibly carcinogenic. The ability to crosslink and produce microspheres without chemical crosslinking is an advantage that eliminates the use of harsh crosslinking agents. Physical methods of crosslinking include radiation (ultraviolet, E-beam, gamma, and others) as well as freeze/thaw methods.

A frequent problem in the production of microspheres in solution is the leaching and solubility of the microsphere prior to crosslinking or with incomplete pre-crosslinking. From the time of formation of the microsphere until it is subjected to irradiation for sterility, as well as for crosslinking, a degree of solubility and leaching of the spheres into the solvent (saline or water) is a problem. When the suspended spheres are ultimately irradiation sterilized (e.g. by E beam, electron beam), the leached material in solution is also crosslinked and a gel and/or precipitate is produced which impairs the clarity of the solution and produces suspended particles, making the material unsuitable for use. This is especially, though not exclusively, seen with polyvinyl alcohol microspheres since they are soft and soluble prior to crosslinking. In order to obviate or mitigate this phenomenon, a specific proprietary process has been discovered which is described in this patent application.

The following points outline the steps of one embodiment of the process of the present invention:
Production of microspheres
   Polymer Solution preparation (e.g. polymer mixing and dissolving in water)
   Polymer Emulsification (e.g. water/oil/water colloid plus shear separation)
   Polymer Drying (Removal of Excess moisture),
   Oil Removal
   Seiving (e.g. calibration by size)
   Re-suspension in final solution
      Incomplete or partial crosslinking
      Ultraviolet irradiation (UVB)
      Rinse
      Packaging
   Rapid freezing
      Cold storage
   Irradiation while frozen (e.g. by use of an E beam)
   Final inspection and product testing It is an objective of the invention to provide a method that allows crosslinking of the polyvinyl alcohol (PVA) polymer to render it insoluble in water or other fluid carriers, without significant loss or change to its other inherent properties, in particular, flexibility, compressibility, softness, and fluid absorption capabilities.

It is another objective of the present invention to crosslink polymeric spheres that are suspended in a liquid making them water insoluble without significantly changing their integrity and other physical characteristics, such as flexibility, absorption, compressibility, and shape.

It is a further objective of the present invention to provide a method for processing polymer microspheres from a solution of polymers/copolymers of mixed molecular weights; i.e. high molecular weights and low molecular weights.

It is yet another objective of the present invention to provide a method for processing polymer microspheres wherein the microspheres are rapidly frozen and subsequently irradiated in the frozen state.

It is a further objective of the present invention to crosslink the polymeric spheres or particles without the use of harsh chemicals that may negatively affect the toxicity levels of the polymer material, which would make it unsafe for medical applications such as embolization, implantation within the human and/or animal body, and drug delivery.

It is another objective of the present invention to provide polymer microspheres processed by the methods described herein.

It is another objective of the invention to use the microspheres processed by the methods described herein as tissue fillers, tissue bulking agents, embolization agents, and/or as drug delivery agents in a human and/or animal subject.

It is yet another objective of the invention to provide the microspheres processed by the methods described herein in injectable dosage form for human and/or animal subjects.

It is another objective of the invention to provided microspheres which are substantially free of crosslinking chemicals or other agents used to stabilize polyvinyl alcohol (PVA). The final product (microspheres completely processed by the steps of the invention) tests negative for traces of these chemicals and/or agents.

It is a further objective of the invention to provide methods for replacing or supplementing tissue volume via administration of the microspheres processed by the methods described herein to a human or animal subject.

It is a further objective of the invention to provide methods for occluding blood vessels via administration of the microspheres processed by the methods described herein to a human or animal subject.

It is yet another objective of the invention to provide a method for delivering a bioactive agent to a human or animal subject in need thereof by loading the microspheres processed by the methods described herein with the bioactive agent and administering the microspheres loaded with the bioactive agent to the human or animal subject.

Another objective of the invention is to provide microspheres for use in tissue augmentation.

It is a further objective of the invention to provide a composition including the described microspheres which can be altered in viscosity and/or elasticity according to the use of the composition.

The above summarizes some of the objectives of the present invention, but is not and should not be construed as an exhaustive list of all of the invention's objectives. Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

The subject matter which is regarded as the invention is particularly pointed out and distinctly claimed in the claims at the conclusion of the specification. The foregoing, and other objects, features, and advantages of the present invention are shown and described in the following detailed description of the preferred embodiments which should be viewed in conjunction with the accompanying process flow drawings. The embodiments (steps) illustrated in the drawings are intended only to exemplify the invention and should not be construed as limiting the invention to the illustrated embodiments (steps).

Each of the flow charts of FIGS. 1-6 illustrates a step in the process for manufacturing polyvinyl alcohol (PVA) microspheres.

DETAILED DESCRIPTION OF THE INVENTION

Figure 1:
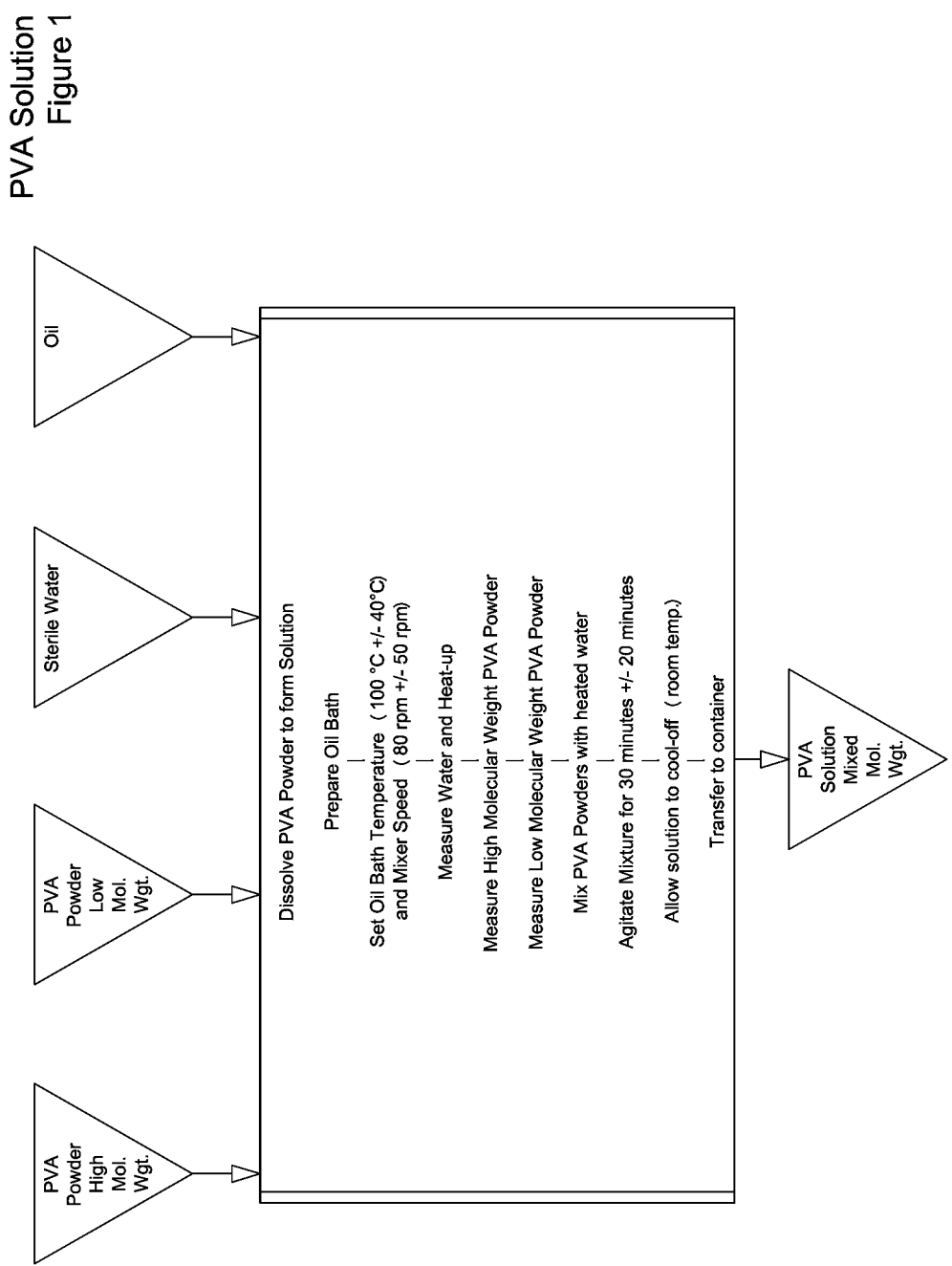
FIG. 1 is a flow chart illustrating preparation of a polyvinyl alcohol (PVA) solution.

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions and methods and any further application of the principles of the invention as described herein, are contemplated as would normally occur to one skilled in the art to which the invention relates.

It is important to note that the embodiments of the invention described below are only examples of some of the uses of the teachings described herein. In general, statements made in the specification do not limit any of the various claimed inventions. Moreover, some statements may apply to some inventive features but not to others. Unless otherwise indicated, singular elements may be in the plural and vice versa with no loss of generality. Similar reference numerals and letters represent similar components and system features throughout the drawings and the written description.

The present invention relates to manufacturing methods for processing polymer microspheres which are suspended in a liquid. The method described in this invention can be used to manufacture polymer microspheres or irregular shape particles, where the polymer or copolymer may be Polyvinyl Alcohol (PVA), Polyvinyl Alcohol Acrylate, Polyvinyl Acetate (PVAc) or other copolymers using PVA.

Microspheres produced by this method are suitable as permanent implants in tissue and are useful for a variety of medical applications, namely: 1) fillers for soft tissue (correct wrinkles, replace/augment tissue volume (cheeks, lips), treat scars, treat lipoatropy); 2) fillers for hard tissue (stabilization/restoration of collapsed/fractured vertebrae); 3) bulking agents for soft tissue (treatment of stress urinary incontinence (SUI), vesicoureteral reflux, vocal cord augmentation); 4) embolization material (neurovascular and/or peripheral vascular occlusion); and 4) drug delivery agents. See Ketie Saralidze et al. "Polymeric Microspheres for Medical Applications" *Materials* 3:3537-3564 2010.

Specifically, the microspheres may be used for embolization of arteriovenous malformations (AVMs), hypervascular tumors, and neoplastic lesions. Additionally, the microspheres may also be used for vascular occlusion of vessels within the neurovascular system when presurgical devascularization is desirable.

The microspheres are particularly useful for embolization of uterine fibroids which are very common benign (non-cancerous) growths that develop in the muscular wall of the uterus. They can range in size from tiny (a quarter of an inch) to larger than a cantaloupe melon. Current treatment options for uterine fibroids include hysterectomy or myomectomy. Both of these are surgically invasive procedures which can result in long recovery times, hospital stays, and surgically-related complications. Embolization with polyvinyl microspheres can provide a minimally invasive alternative to relieve symptomatic uterine fibroids.

The method of the present invention has been demonstrated to minimize or prevent the leaching/solubility problem in processing microspheres. Shortly after formation, separation and calibration, the microspheres are resuspended in the appropriate solution (saline, water, etc.) for ultraviolet irradiation. The spheres are not irradiated dry because when crosslinked or irradiated in that state, they become brittle and hardened which impairs their use, for example, in small vessels where flexibility and deformability are assets. The resuspended spheres are then subjected to ultraviolet irradiation. The irradiation prepares the spheres for transit or warming by partially crosslinking them. In spite of thorough ultraviolet irradiation, the spheres (especially, but not exclusively polyvinyl alcohol (PVA) spheres) still will solubilize, gel and precipitate when subjected to irradiation with no further preparation. This is related to the heat and energy imparted in the initial stages of crosslinking by irradiation. However, if the spheres and the solvent are subjected to rapid freezing, and subsequently irradiated while in the frozen state, the problem is obviated. A step for sterilization of microspheres in a frozen state is not found in the prior art.

It is also noted that the freeze/thaw pre-processing of the microsphere produces a physical change in the sphere that enhances visibility by virtue of increasing the opacification and whiteness of the sphere on a permanent basis. Thus, the microspheres prepared using this process can be utilized with imaging technologies. The freeze/thaw process evokes size changes which must be anticipated in calibrating and separating the spheres. The freeze/thaw cycles can be repeated as needed, but in most cases a single cycle will suffice to prevent gel or precipitate formation.

The following experimental example describes the steps of one embodiment of the process of the present invention. Background information regarding each step of the process is also included.

Method for Processing Polyvinyl Alcohol (PVA) Microspheres

Dissolve PVA & Create PVA Solution:

This step is illustrated in the flow chart of FIG. 1.

Background

Polyvinyl alcohol (PVA) is a biocompatible, non-degradable, and non-absorbable synthetic polymer. Microspheres processed from PVA neither degrade nor are absorbed by tissue. PVA has a long history of use in medical devices, biological and chemical sciences, the food industry, and the pharmaceutical industry. PVA material has over 25 years of clinical use as an implantable material.

Polyvinyl Alcohol (PVA) is a water soluble resin that easily dissolves in water, but solubility depends on the degree of polymerization and degree of hydrolysis.

In general degree of polymerization and hydrolysis affects solubility in water as follows:

The lower the degree of polymerization the easier it dissolves in water,

Partially hydrolyzed grades dissolve easier than fully hydrolyzed grades.

The PVA powders used by Scion CV (assignee) have a combination of low and high degrees of polymerization (typical: 700-4200) with high degrees of hydrolysis (typical 98%+). As a result, the dissolution of the PVA powder in water is aided with heat and agitation, as recommended by the PVA manufacturer.

Polyvinyl Alcohol (PVA) Solution

The PVA powders are dissolved in sterile water to obtain a 8% PVA solution, by weight.

One formulation used is:

790 g sterile water

Low Molecular Weight (LMW) PVA powder: 28 g

High Molecular Weight (HMW) PVA powder: 42 g

LMV PVA is considered as having a molecular weight in a range from about 10,000 to 100,000 daltons and HMV PVA is considered as having a molecular weight in a range from about 100,000 daltons to 250,000 daltons.

The ratio of 3 parts HMW PVA to 2 parts LMW PVA (by weight) on a 8% PVA solution results in a final product (spheres) with adequate shape, surface porosity, flexibility, and compressibility.

By adjusting the percentages and ratios of HMW PVA to LMW PVA, the sphere size, surface porosity, flexibility, and compressibility can be affected up or down, as follows:

Higher percent PVA solution (>8%) results in larger spheres, typically greater than 1 mm (1000 μm);

Lower percent PVA solution (<8%) results in smaller spheres, typically below 50 μm;

More HMW PVA content with less LMW PVA content results in less flexibility and compressibility; and Less HMW PVA content with more LMW PVA content results in more flexibility and compressibility.

Component Preparations:

Low Molecular Weight (LMW) Polyvinyl Alcohol (PVA) and High Molecular Weight (HMW) Polyvinyl Alcohol powders are weighed and mixed manually in a container.

Sterile water is weighed and heated above 80° C., while being agitated inside a beaker in a hot-oil bath. The oil bath temperature can be set in a range from about 100° C.+/−40° C. The mixing (agitation speed) can be set in a range from about 80 rpm+/−50 rpm.

Synthesis:

PVA powder(s) are slowly added to heated water, while maintaining agitation, to dissolve PVA powder. Agitation and heat are maintained for a time period of about 30 minutes+/−20 minutes (until all solids have been dissolved). The solution is then allowed to cool to room temperature before being transferred into a container.

Figure 2:
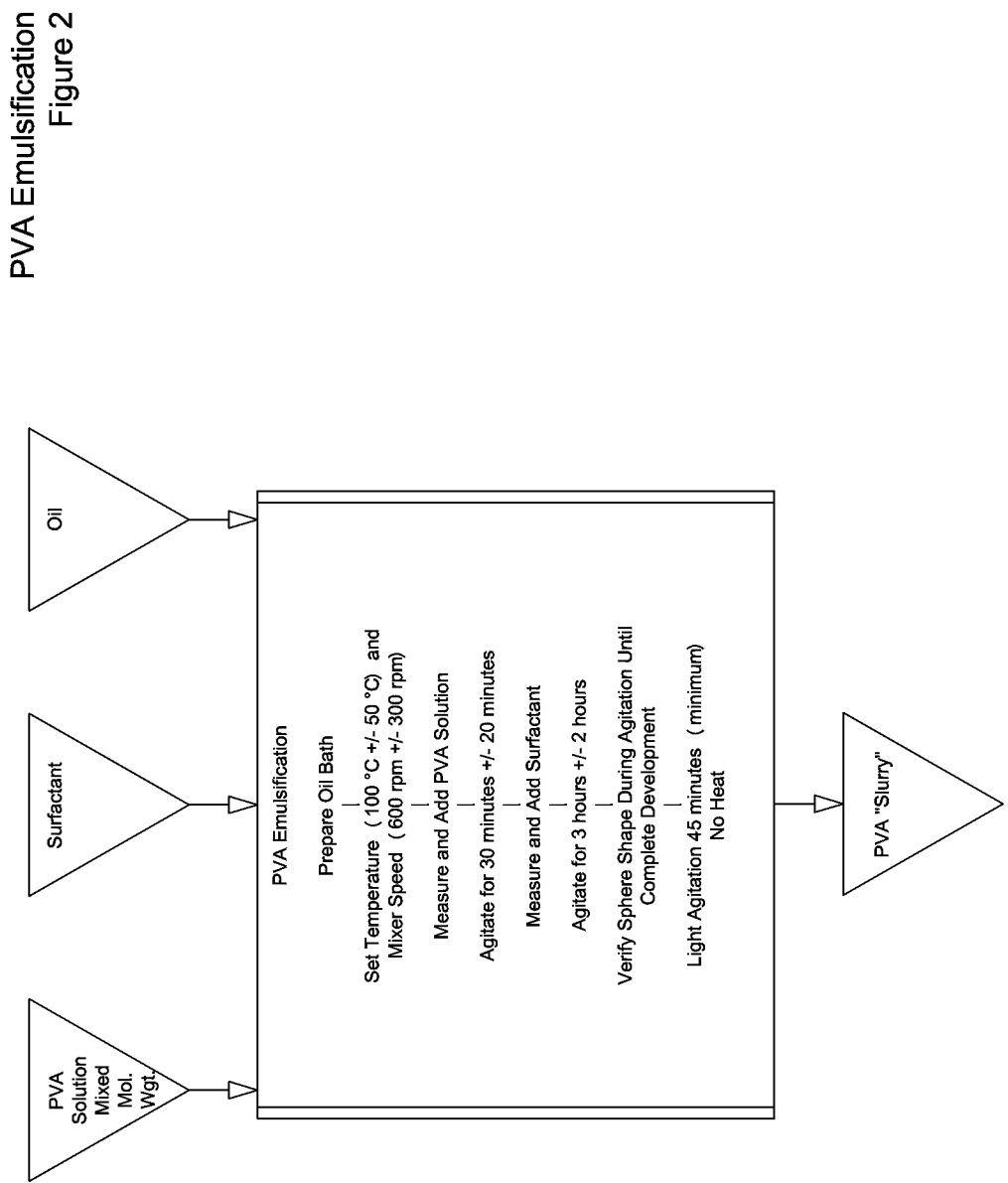
FIG. 2 is a flow chart illustrating polyvinyl alcohol (PVA) emulsification.

Emulsify PVA & Create Spheres:

This step is illustrated in the flow chart of FIG. 2.

Background

The microspheres are generated using Water-in-Oil (W/O) emulsion. That is, discrete water droplets dispersed in a continuous oil phase. The PVA solution consists of at least 90% water with 10% or less PVA.

By definition, an emulsion is a two-phase system consisting of two non-miscible liquids, one of which is dispersed as finite globules in the other, i.e. PVA solution dispersed in oil. Emulsions are thermodynamically unstable. Eventually the dispersed globules will coalesce to reduce the interfacial area to reduce the interfacial free energy of the system. Thus, an emulsifying agent is added to the emulsion to facilitate its production and slow down its inevitable destruction (coalescence of the emulsion).

Scion CV (assignee) uses a hydrophobic, non-ionic surfactant (Sorbitan Monostearate or Span), to help maintain the emulsification process while all the appropriate conditions/parameters are maintained (i.e. heat, agitation and time).

The formation of PVA spheres in the W/O emulsion is based on the fact that spheres are considered the smallest geometrical shape with the fewest molecules. As a result, in a water-in-oil emulsion, spheres of PVA solution (mainly water) will form almost immediately when added to the oil phase, together with the help of the heat and agitation of the oil.

Component Preparations:

The oil bath temperature can be set in a range from about 100° C.+/−50° C. The mixing (agitation speed) can be set in a range from about 600 rpm+/−300 rpm.

Mineral Oil is measured (volumetric) and heated under light agitation,

PVA solution is measured (volumetric) and added to the heated and agitated oil—agitation increased; agitation is for a time period of about 30 minutes+/−20 minutes, Sorbitan Monostearate (surfactant) added to the heated and agitated emulsion (PVA/Oil) system; agitation is for a time period of about 3 hours+/−2 hours, Sorbitan is quickly dissolved in the oil (hydrophobic surfactant).

Sphere shape development is verified during agitation until complete development and then the heat is removed and the emulsification is lightly agitated for at least 45 minutes resulting with a PVA slurry.

Synthesis:

As indicated above the PVA solution quickly goes into droplet/spherical form when added to the oil under agitation and heated conditions.

The addition of the emulsifier helps maintain the emulsion in equilibrium while the appropriate combination of heat, agitation and time removes (by evaporation) the excess water from the PVA droplets/spheres.

As the water evaporates from the PVA spheres, suspended in oil, the density of the spheres gradually changes as the spheres lose water and start to solidify, while in the emulsification system.

Once the density of the spheres reaches a point where the majority of the water has evaporated and the spheres are partially solidified, heat is removed from the system and agitation is reduced to start the cooling-off period.

During this time the emulsifying agent re-solidifies back into its original granular form that can be easily seen dispersed in the oil among the partially solidified spheres.

Figure 3:
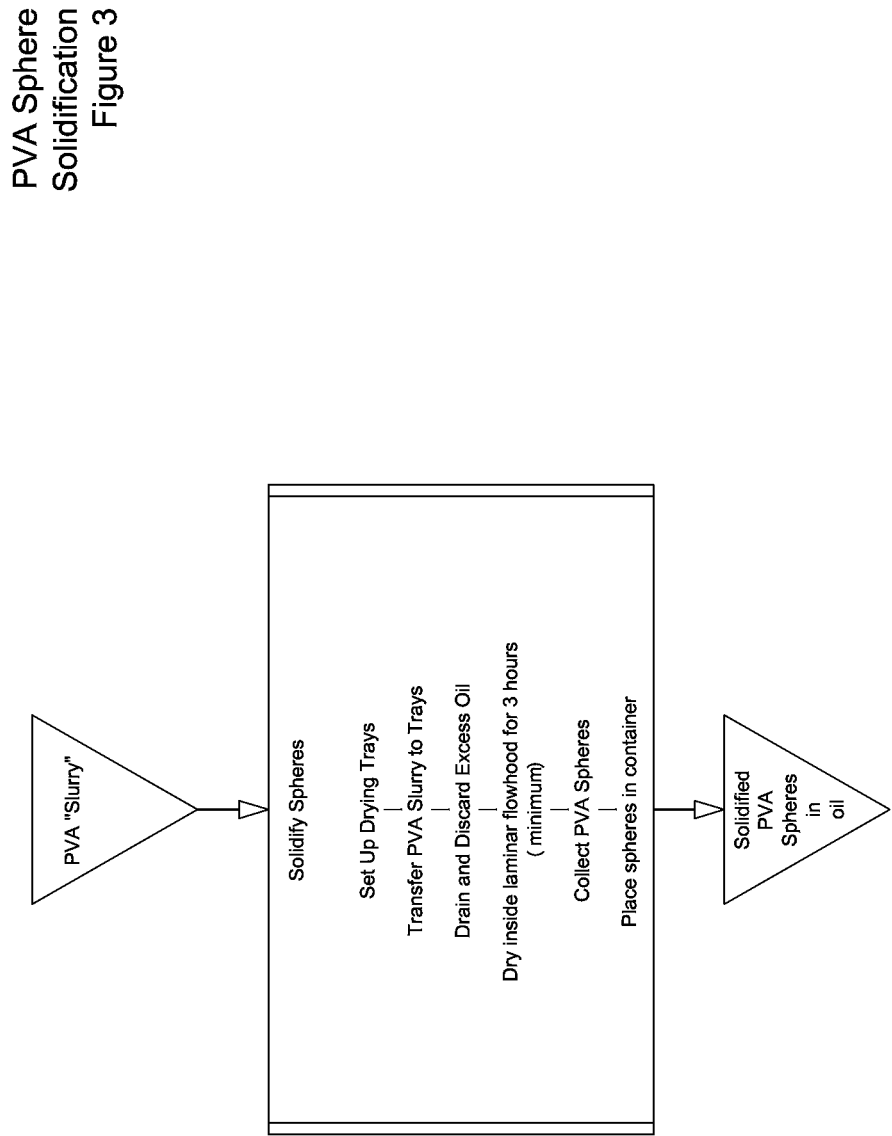
FIG. 3 is a flow chart illustrating polyvinyl alcohol (PVA) sphere solidification.

Solidify Spheres:

This step is illustrated in the flow chart of FIG. 3.

Background (Solidify Spheres from the slurry):

As noted in the previous step, the Emulsification process is stopped once the spheres have reached a partially solid phase, but the spheres are still soft. Final solidification of the spheres occurs by exposing the spheres to air.

Component Preparations:

PVA spheres, partially solidified, together with the oil and emulsifying agent are removed from the emulsion tank and placed on a flat surface (tray) where they are spread out over a large surface area to expose them to air. Excess oil (and surfactant) is removed from the tray until the appropriate ratio of sphere and oil is achieved. The spheres are dried in a laminar flowhood for at least 3 hours.

Synthesis:

Final solidification of the spheres occurs by exposing the PVA spheres to air over a period of time.

After a minimum of 8 hours, the spheres are collected and stored in vials for further processing.

Figure 4:
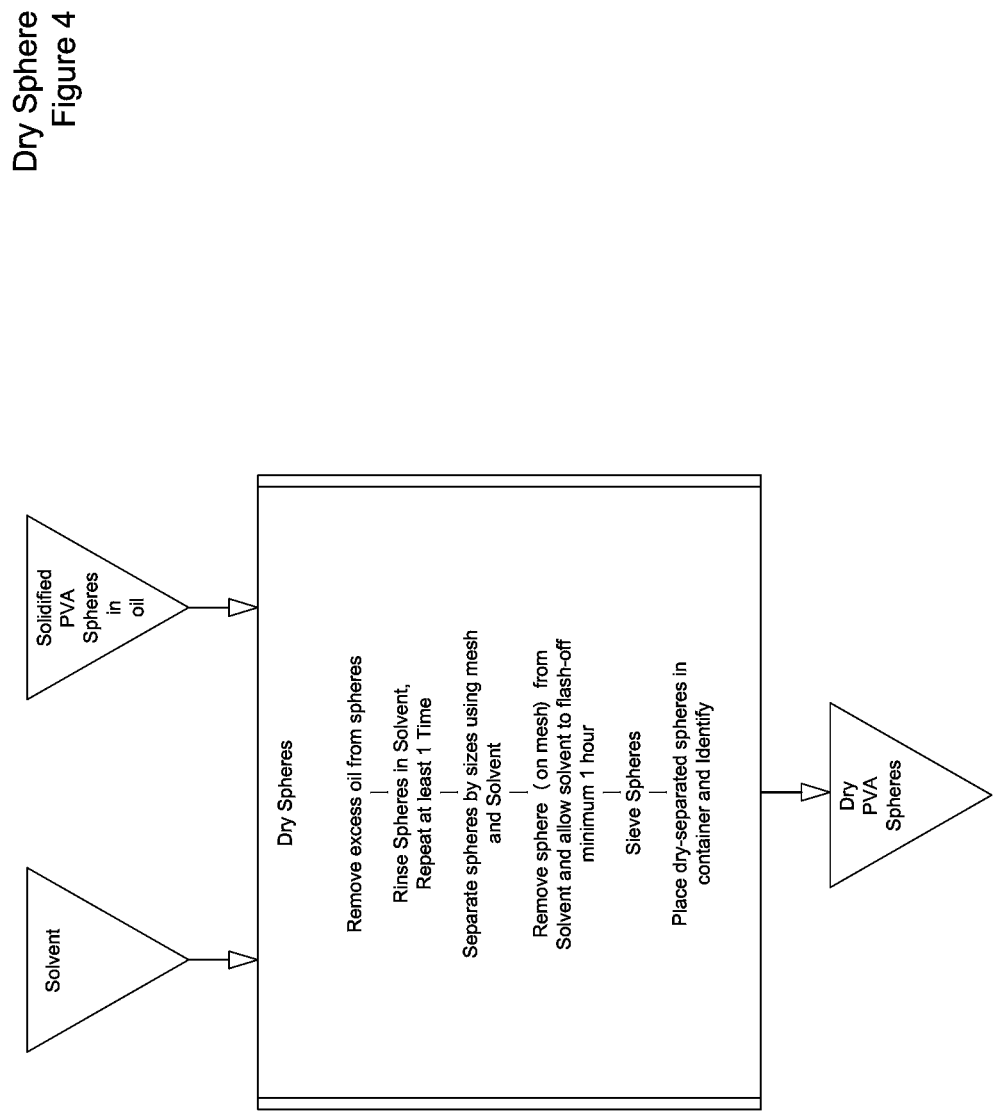
FIG. 4 is a flow chart illustrating polyvinyl alcohol (PVA) drying.

Remove Oil and Dry Spheres:

This step is illustrated in the flow chart of FIG. 4.

Background

At this stage, the PVA spheres, stored in a slurry of solid PVA spheres, oil and surfactant, need to be separated from this oil and surfactant. To do this a mild, but effective solvent separates the oil and surfactant from the PVA spheres, without adversely reacting with the PVA spheres or leaving excessive residues.

Concurrently, the spheres are separated by size via a sieving process according to the final size ranges of the final product configuration (i.e. 100 to 1100 micron size). The spheres may also be sorted according to the diameter of the inner lumen of the device that will be used to deliver the spheres.

TABLE 1

| Size Range of Microspheres (μm) | Recommended Delivery Catheter Inner diameter (mm) |
|---|---|
| 100-300 | 0.021-0.53 |
| 300-500 | 0.021-0.53 |
| 500-700 | 0.021-0.53 |
| 700-900 | 0.027-0.69 |
| 900-1100 | 0.035-0.89 |

Component Preparations:

PVA spheres slurry from solidification step

Isopropanol—99% pure solvent

Synthesis:

The PVA spheres slurry is repeatedly washed and rinsed with the alcohol to remove and carry away oil and surfactant residues. This wash/rinse is repeated at least one time.

The washing and rinsing process is performed by putting the PVA spheres through a series of meshes designed to capture and separate spheres by sizes, while allowing the smaller particles (i.e. surfactant particle residues) and oil resides to be carried away by the solvent.

Following the Isopropanol washes, excess solvent is removed from the spheres by placing the spheres under forced and lightly heated air for a minimum of 1 hour to allow the Isopropanol residuals to flash-off the surface of the spheres.

Next, the dry/clean spheres are sieved; i.e. the spheres are put through a series of calibrated meshes to perform the final size separation. The dry/clean and size-separated spheres are collected in containers and stored for further processing.

Figure 5:
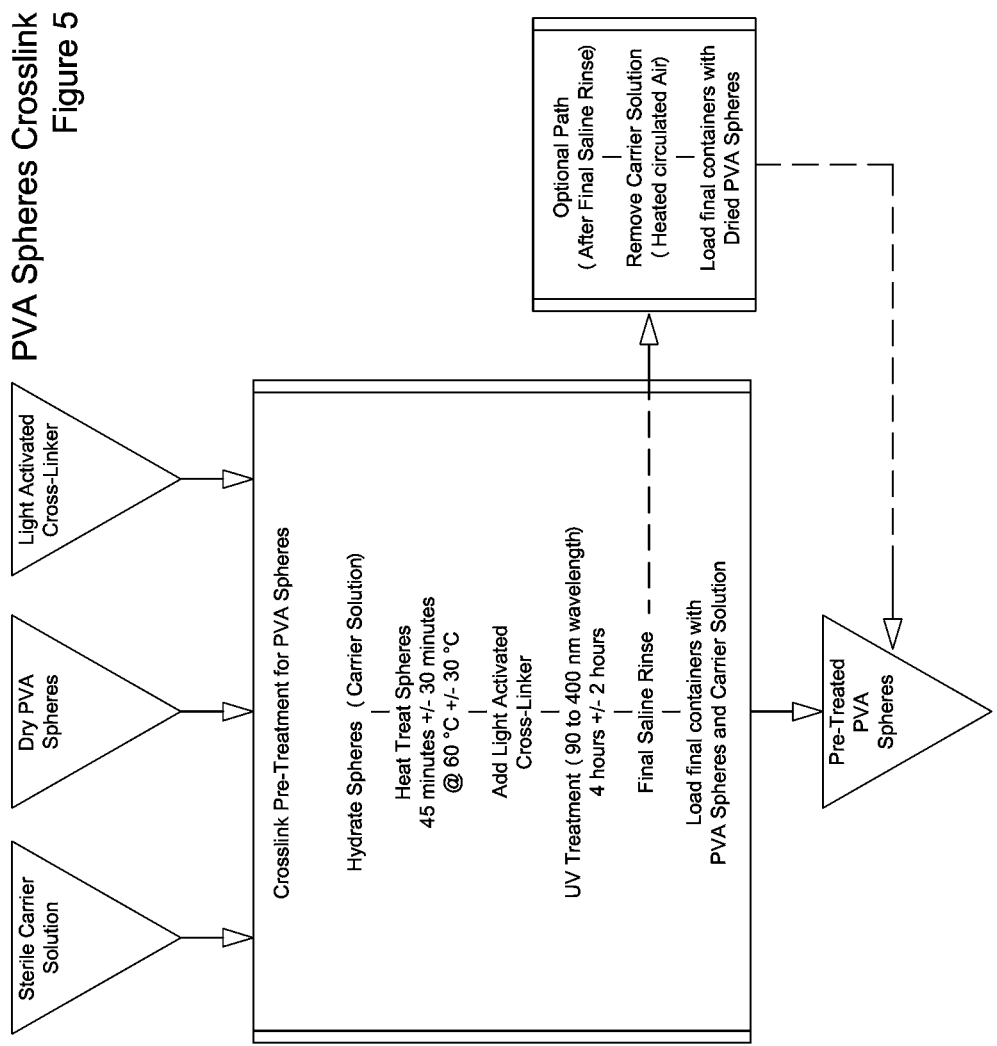
FIG. 5 is a flow chart illustrating a crosslink pre-treatment for the polyvinyl alcohol (PVA) spheres.

Rinse, Separate and Dry:

This step is illustrated in the flow chart of FIG. 5.

Hydrate Sphere:

Background

In preparation for final product packaging configuration, the spheres are hydrated with 0.9% Sodium Chloride (carrier solution).

Component Preparations:

Dry/Clean size-separated spheres from previous manufacturing process

Sterile 0.9% Sodium Chloride

Synthesis:

Sterile 0.9% Sodium Chloride (saline) is poured onto dry/clean spheres for hydration.

Spheres are completely submerged in saline for a minimum of 5 minutes to allow complete hydration of the spheres (from outer surface to core). This process is repeated at least three times with fresh saline to ensure spheres are completely hydrated. The hydrated spheres are collected into a sealed container and moved to the next processing step.

Sphere Heat Treat:

Background

PVA is an excellent hydrophilic material. As a result, PVA spheres experience diametrical growth during the hydration process and during further processing when heat is applied to the spheres.

The spheres are subjected to a heat treatment process to further grow/expand the spheres to the desired size range. The process parameters that influence the growth/expansion of the sphere are the process temperature and time.

The final size of the spheres is determined through controlling and adjusting the sieving, separation, and hydration steps.

Component Preparations:
Hydrated PVA spheres
Synthesis:
Hydrated PVA spheres are placed inside a calibrated oven, inside sealed containers, to prevent unwanted contamination. Heat treatment is performed for a time period of 45 minutes+/−30 minutes at a temperature of 60° C.+/−30° C.

PVA Sphere Ultraviolet-Induced Cross-Linking:

Background

PVA is inherently a water soluble polymer. As a result, since the microspheres are packaged and stored in a water-based solution (saline) there is a need to modify the spheres to make the PVA polymer water-insoluble, after the spheres are made and processed.

Cross-linking of PVA, as a way to make it water-insoluble, has been successfully performed and is well documented in the literature. Because of the intended use of the microspheres as an implant material, Scion CV (assignee) decided not to use any potentially harmful reagents, such as formaldehyde and/or boric acid to cross-link the PVA, since traces of these materials could potentially remain in the final product.

Instead, modification of the microspheres (M-Bolus™ Microspheres) to make them water-insoluble has been achieved by Ultraviolet (UV) radiation in the presence of Sodium Benzoate, as a sensitizer or photo-initiator. In this process, cross-linking is always accompanied by photolysis (decomposition) of the sensitizer. In the absence of the sensitizer, no cross-linking occurs.

The actual mechanism of PVA cross-link using this method has been studied in the literature by several researchers who suggest that a free radical arising from the photolysis of Sodium Benzoate abstracts a tertiary hydrogen atom from the polymer chain (at a C-H linkage) to yield a polymeric radical. This radical reacts with O-H group giving rise to the formation of ether bonds between polymeric chains, leading to the cross-linking and insolubility of the PVA.

Component Preparations:
Hydrated and Heat-treated PVA spheres
Sodium Benzoate Solution: A solution of Sodium Benzoate is prepared using 0.9% Sodium Chloride.
Synthesis:
Hydrated and heat-treated PVA spheres are mixed with the Sodium Benzoate solution (light activated cross linker) and placed inside a UV chamber at a specific wavelength (90 to 400 nm), inside sealed containers, to prevent unwanted contamination.

The PVA spheres are exposed to UV light for a time period of 4 hours+/−2 hours.

Movement of the spheres is performed during the UV exposure to ensure all spheres and solution are sufficiently exposed to the UV light (avoid shadowing effect from other spheres within container).

UV treated spheres are then transferred to the next processing station for final saline rinse.

Final Sphere Rinse:
Background
In preparation for product packaging (loading) into syringes, the spheres are thoroughly rinsed with 0.9% Sodium Chloride (saline) to remove traces of the sodium benzoate added during the UV process and any other reagent traces used during the manufacturing of the spheres not fully eliminated during the previous steps. Possible traces of mineral oil, surfactant and/or Isopropanol that may still be remaining in the spheres are eliminated with this final saline rinse.

Component Preparations:
UV treated spheres from previous manufacturing process
Sterile 0.9% Sodium Chloride
Synthesis:
Spheres are removed from their closed containers and placed in a larger container. Once the spheres settle to the bottom of the container (after several minutes), the majority of the saline containing the added sodium benzoate is discarded and replaced with "fresh" Sterile 0.9% Sodium Chloride (saline).

Once the spheres resettle to the bottom of the container the saline is once again removed and replaced with additional "fresh" saline. This process is repeated a minimum of ten times (10), with at least 3000 ml of "fresh" saline for every 50 ml of spheres.

Rinsed/cleaned spheres (pre-treated spheres) in a carrier solution are then transferred to the next processing station for further processing.

Optionally, the carrier solution can be removed after the final saline rinse with heated circulated air and then the dried spheres transferred to a container for further processing.

Figure 6:
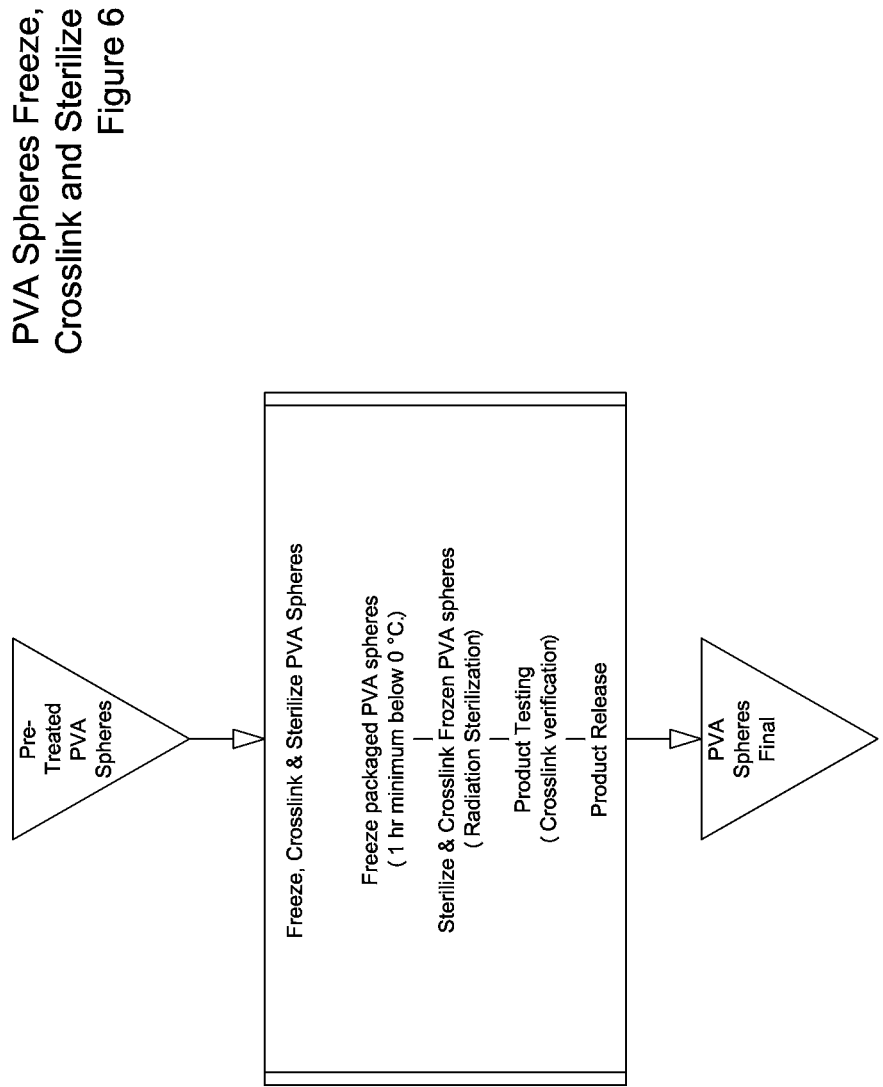
FIG. 6 is a flow chart illustrating freezing, crosslinking, and sterilizing polyvinyl alcohol (PVA) microspheres.

Load Syringes with Spheres and Saline:
This step is illustrated in the flow chart of FIG. 6.

Background

Rinsed/cleaned pre-treated spheres are now ready for packaging into syringes.
Component Preparations:
Rinsed/cleaned spheres from previous manufacturing process
Sterile 0.9% Sodium Chloride
Syringe
Printed Syringe label
Syringe pouch
Synthesis:
The loading and packaging steps consist of the following steps:
  Syringe loading: Syringes are loaded with 2 ml of spheres and 3 ml of saline.
  Syringe labeling: Syringe labels applied to syringe barrels.
  Pouch loading: Syringe (1×) placed inside pouch (1×).
  Pouch sealing: Pouch is heat sealed to generate product sterile barrier.
The syringe used may be a 20 ml polycarbonate syringe with luer-lock threads. If the microspheres are not visible under fluoroscopy, they (the microspheres) can be delivered in a diluted mixture of radiopaque contrast media. The size of the syringe allows for mixing with diluted contrast media prior to use.

Final Labeling, Packaging and Boxing:
Background
Pouched/loaded syringes are now ready for final labeling, packaging and boxing.

Component Preparations:
Pouched/Loaded syringes from previous manufacturing process
Printed carton label
Instructions for Use (IFU)
Assembled Carton
Shipper Box
Synthesis:
The final packaging steps consist of the following steps:
Carton loading: Two pouched syringes are loaded into a carton.
IFU Inserted: IFU placed inside Carton with pouched syringes.
Carton Labeling: Carton label applied to carton.
Boxing: loaded cartons are placed in a shipper box and sealed with tape.
Ship to Sterilizer:
Boxed syringes (in 2-pack cartons) are now ready for final shipment to sterilization.
Prior to irradiation (sterilization), the packaged microspheres are frozen for a time period of at least 1 hour at a temperature below 0° C. The frozen microspheres are then sterilized and crosslinked via radiation (i.e. E-beam (electron beam) radiation).

At this point, the crosslinking can be verified and the finished product tested for quality.

One parameter that may be test is compressibility of the microspheres. This test is carried out by compressing the spheres and measuring the time it takes (the spheres) to recover their original diameter. For example, in one test conducted, the spheres were compressed to 40% of their original diameter and took approximately 1.7 seconds to recover 90% of their original diameter. Full recovery took less than a minute.

Additionally, a material chemical analysis could be performed on the spheres. The results of this analysis can be used for comparison with known polymer products. For example, the microspheres described herein were found to contain polyvinyl alcohol (PVA) which was substantially free of crosslinking chemicals or other agents used to stabilize polyvinyl alcohol (PVA) when compared to other polymer products which were found to include chemical additives and stabilizing agents.

In summary, the microspheres processed from the described methods have a smooth, lightly porous surface (with no abrupt discontinuities) with hydrophilic characteristics. They are soft and flexible allowing them to be compressed/deformed (30%-50% compressible, minimum 30% without rupture, resilient) as they travel through the lumen of a delivery device (i.e. catheter) or through the vasculature. In addition, the microsphere's shape and relatively smooth surface help to minimize aggregation and clumping in the catheter and/or vascular lumen, enhancing delivery to the target site.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The polymeric microspheres, processes, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. A method for producing polymer microspheres, the method comprising:
preparing a solution including at least two polymers or copolymers;
preparing an emulsification of the solution;
forming solidified microspheres from the emulsification;
drying the solidified microspheres;
separating the solidified microspheres according to size;
pre-treating the separated, solidified microspheres for crosslinking;
freezing the pre-treated microspheres; and
crosslinking and sterilizing the frozen, pre-treated microspheres by applying radiation; wherein the crosslinking is carried out such that the polymer microspheres produced are substantially free of crosslinking chemicals or other agents used to stabilize polymers or copolymers; wherein preparing solution includes adding a polymer or copolymer having a low molecular weight and a polymer or copolymer having a high molecular weight such that the resulting solution has a mixture of polymers or copolymers of both high and low molecular weights.

2. The method according to claim 1, wherein the pre-treating includes hydrating the microspheres, heating the hydrated microspheres, adding a photo initiator to the hydrated microspheres, and applying ultraviolet treatment to the hydrated microspheres.

3. The method according to claim 1, wherein preparing the solution includes selecting at least one polymer or copolymer from the group consisting of polyvinyl alcohol (PVA), polyvinyl alcohol acrylate (PVA-A), and polyvinyl acetate (PVAc).

4. The method according to claim 3, wherein preparing the solution includes selecting a polyvinyl alcohol (PVA) which is at least about 98% hydrolyzed.

5. The method according to claim 1, wherein the low molecular weight polymer or copolymer has a molecular weight in a range from about 10,000 to 100,000 daltons and the high molecular weight polymer or copolymer has a molecular weight in a range from about 100,000 to 250,000 daltons.

6. The method according to claim 1, wherein preparing the solution includes adding three parts of the high molecular weight polymer or copolymer to two parts of the low molecular weight polymer or copolymer by weight.

7. The method according to claim 1, further including hydrating the microspheres and packing the hydrated microspheres in injectable dosage form.

8. The method according to claim 7, further including adding a contrast agent to the microspheres after packing.

9. The method according to claim 1, wherein the separating includes separating the solidified microspheres by sizes in a range of about 100 μm to 1100 μm.

10. The method according to claim 1, wherein the separating includes separating the solidified microspheres by size corresponding to an inner diameter of a delivery device to be used for administration of the microspheres to a subject in need thereof.

11. The method according to claim 1, wherein the freezing includes freezing for a time period of at least one hour at a temperature below 0° C.

12. The method according to claim 1, wherein the crosslinking and sterilization of the frozen microspheres includes applying e-beam (electron-beam) radiation.

13. A method for producing polymer microspheres, the method comprising:
preparing a solution by mixing polyvinyl alcohol (PVA) which is at least about 98% hydrolyzed and water;
preparing an emulsification of the solution by adding a surfactant and mineral oil;
forming solidified microspheres from the emulsification;
drying the solidified microspheres;
separating the solidified microspheres according to size;
pre-treating the separated, solidified microspheres for crosslinking; the pre-treating including hydrating the microspheres, heating the hydrated microspheres, adding a photo initiator to the hydrated microspheres, and applying ultraviolet treatment to the hydrated microspheres;
freezing the pre-treated microspheres; and
crosslinking and sterilizing the frozen, pre-treated microspheres by applying e-beam (electron beam) radiation; wherein the crosslinking is carried out such that the polymer microspheres produced are substantially free of crosslinking chemicals or other agents used to stabilize polyvinyl alcohol (PVA).

14. The method according to claim 13, wherein preparing the solution includes adding a polyvinyl alcohol (PVA) having a low molecular weight and a polyvinyl alcohol (PVA) having a high molecular weight such that the resulting solution has polyvinyl alcohols of both high and low molecular weights.

15. The method according to claim 14, wherein the low molecular weight polyvinyl alcohol (PVA) has a molecular weight in a range from about 10,000 to 100,000 daltons and the high molecular weight polyvinyl alcohol (PVA) has a molecular weight in a range from about 100,000 to 250,000 daltons.

16. The method according to claim 14, wherein preparing the solution includes adding three parts of the high molecular weight polyvinyl alcohol (PVA) to two parts of the low molecular weight polyvinyl alcohol (PVA) by weight.

17. The method according to claim 13, further including hydrating the microspheres and packing the hydrated microspheres in an injectable dosage form.

18. The method according to claim 17, further including adding a contrast agent to the microspheres after packing.

19. The method according to claim 13, wherein the separating includes separating the solidified microspheres by size in a range of about 100 μm to 1100 μm.

20. The method according to claim 13, wherein the separating includes separating the solidified microspheres by size corresponding to an inner diameter of a delivery device to be used for administration of microspheres to a subject in need thereof.

21. The method according to claim 13, wherein the freezing includes freezing for at least one hour at a temperature below 0° C.

22. The method according to claim 13, wherein the preparing an emulsification includes adding a sorbitan monostearate surfactant.

23. The method according to claim 13, wherein the adding a photo initiator to the hydrated microspheres includes adding sodium benzoate.

24. Polymer microspheres produced according to the method of claim 1.

25. Polymer microspheres produced according to the method of claim 13.

26. Polymer microspheres produced according to the method of claim 1, wherein the polymer microspheres are substantially free of crosslinking chemicals or other agents used to stabilize polyvinyl alcohol (PVA).

27. A method for replacing tissue volume comprising administering the polymer microspheres of claim 26 to a subject in need thereof.

28. The method of claim 27, wherein the tissue is selected from the group consisting of soft tissue in a facial area, vocal fold tissue, and urinary tract tissue.

29. A method for occluding a vessel comprising administering the polymer microspheres of claim 26 to a subject in need thereof.

30. The method of claim 29, wherein the vessel is a blood vessel.

31. A method for delivering a bioactive agent to a subject in need thereof comprising loading the microspheres of claim 26 with the bioactive agent and administering the microspheres loaded with the bioactive agent to the subject.

* * * * *